(12) United States Patent
 Zhou et al.

(10) Patent No.: US 11,123,082 B2
(45) Date of Patent: Sep. 21, 2021

(54) ATRIAL APPENDAGE CLIP DELIVERY SYSTEM

(71) Applicant: Beijing Med-Zenith Medical Scientific Corporation Limited, Beijing (CN)

(72) Inventors: Qingliang Zhou, Beijing (CN); Danian Ke, Beijing (CN); Jian Meng, Beijing (CN); Xiaofang Liu, Beijing (CN)

(73) Assignee: Beijing Med-Zenith Medical Scientific Corporation Limited, Beijing (CN)

( * ) Notice: Subject to any disclaimer, the term of this patent is extended or adjusted under 35 U.S.C. 154(b) by 43 days.

(21) Appl. No.: 16/322,934

(22) PCT Filed: Dec. 29, 2016

(86) PCT No.: PCT/CN2016/112824
§ 371 (c)(1),
(2) Date: Feb. 2, 2019

(87) PCT Pub. No.: WO2018/032692
PCT Pub. Date: Feb. 22, 2018

(65) Prior Publication Data
US 2019/0183511 A1   Jun. 20, 2019

(30) Foreign Application Priority Data
Aug. 16, 2016   (CN) .......................... 201610677809.7

(51) Int. Cl.
*A61B 17/128* (2006.01)
*A61B 17/00* (2006.01)

(52) U.S. Cl.
CPC .... *A61B 17/1285* (2013.01); *A61B 17/00234* (2013.01); *A61B 17/128* (2013.01); *A61B 2017/00243* (2013.01)

(58) Field of Classification Search
CPC .............. A61B 17/128; A61B 17/1285; A61B 17/00234; A61B 2017/00243; A61B 2017/1225
See application file for complete search history.

(56) References Cited

U.S. PATENT DOCUMENTS 9,814,462 B2 *  11/2017  Woodard, Jr. ..... A61B 17/0643
2006/0020271 A1   1/2006  Stewart et al.
(Continued)

FOREIGN PATENT DOCUMENTS

CN         203074795 U    7/2013
CN         203328756 U    12/2013
(Continued)

OTHER PUBLICATIONS

JP first Office Action dated Dec. 9, 2019 re: Application No. 2019-506151, pp. 1-3, citing: CN203074795U and JPA2012-035075.
(Continued)

*Primary Examiner* — Katrina M Stransky
*Assistant Examiner* — Mohammed S Adam
(74) *Attorney, Agent, or Firm* — Gang Yu

(57) ABSTRACT

Disclosed is an atrial appendage clip delivery system, which includes a handle shell, a push rod, a connection pipe and a support base; a passage is provided in the handle shell along a length direction; one end of the push rod is slidably disposed in the passage; the support base is provided with a mounting window for mounting an atrial appendage clip; the atrial appendage clip includes a first clip arm and a second clip arm capable of opening in parallel or closing; the handle shell, the connection pipe and the support base are sequentially connected and communicate; the first clip arm or the second clip arm is fixedly connected with an upper side or a lower side of the mounting window; the second clip arm or the first clip arm is movably connected with the lower side or the upper side of the mounting window.

11 Claims, 3 Drawing Sheets

(56) References Cited

U.S. PATENT DOCUMENTS

| | | |
|---|---|---|
| 2012/0109161 A1 | 5/2012 | Privitera et al. |
| 2013/0190777 A1 | 7/2013 | Hughett et al. |
| 2015/0173767 A1 | 6/2015 | Monti et al. |
| 2015/0320426 A1 | 11/2015 | Cosgrove, III et al. |
| 2016/0151072 A1 | 6/2016 | Hughett, Sr. et al. |

FOREIGN PATENT DOCUMENTS

| | | |
|---|---|---|
| CN | 104490449 A | 4/2015 |
| CN | 105193471 A | 12/2015 |
| CN | 106073858 A | 11/2016 |
| CN | 106137302 A | 11/2016 |
| CN | 206275718 U | 6/2017 |
| EP | 2502578 A1 | 9/2012 |
| JP | 2001514563 A | 9/2001 |
| JP | 2012035075 A | 2/2012 |
| WO | 2013025841 A1 | 2/2013 |

OTHER PUBLICATIONS

JP Decision of Rejection dated May 18, 2020 re: Application No. 2019-506151, pp. 1-4.
EP first search report dated Apr. 2, 2020 re: Application No. 16913444.2, pp. 1-8.
IN first office action dated Feb. 10, 2021 re: Application No. 201947009394, pp. 1-5.

* cited by examiner

ATRIAL APPENDAGE CLIP DELIVERY SYSTEM

TECHNICAL FIELD

Embodiments of the present disclosure relate to a technical field of medical appliances, and in particular to an atrial appendage clip delivery system.

BACKGROUND

Atrial fibrillation is one of the most common arrhythmias clinically. A cerebral stroke caused by the atrial fibrillation has a very serious consequence, with the death rate and the disability rate up to 70%. For a patient suffering from valvular atrial fibrillation, 57% of atrial thrombi are from a left atrial appendage. For a patient suffering from non-valvular atrial fibrillation, 90% of left atrial thrombi are from the left atrial appendage. Even though a sinus rhythm is restored, due to stunned shrinkage of the left atrial appendage, a thrombus may still be formed.

At present, three methods are provided mainly to clinically prevent an atrial fibrillation ischemic stroke. The first method is to take an anticoagulant drug such as warfarin. However, the warfarin has a hemorrhage risk and many contraindications and must be monitored frequently, and thus is difficult to put into a clinical application. Besides, it is possible for the warfarin to cause osteoporosis and soft tissue necrosis. The second method is to directly excise or ligate an atrial appendage during a heart surgery. A main defect of such method is the low complete closure rate of the left atrial appendage, and it is shown in a previous study that the success rate for completely excising the left atrial appendage is about 80% at maximum. The third method is to close the left atrial appendage via an appliance and is a percutaneous interventional atrial appendage occlusion product; but such a method has a complex operation and a high risk, and the safety and the effectiveness are to be verified.

SUMMARY (1) Technical problems to be solved

An objective of the present disclosure is to design an atrial appendage clip delivery system which is safe and effective, and is convenient to operate, so that an atrial appendage clip is placed from an outside of a heart to a root of a left atrial appendage to close the left atrial appendage in a thoracotomy or minimally invasive surgery.

(2) Technical solutions

In order to solve the above technical problems, the present disclosure provides an atrial appendage clip delivery system, which includes a handle shell, a push rod, a connection pipe and a support base.

A passage is provided in the handle shell along a length direction of the handle shell.

One end of the push rod is located in the passage, and is slidably and cooperatively connected with the passage.

The connection pipe is a hollow pipeline; one end of the connection pipe is connected with the handle shell, and the other end of the connection pipe is connected with the support base.

The support base is provided with a mounting window for mounting an atrial appendage clip.

The atrial appendage clip includes a first clip arm and a second clip arm capable of opening in parallel or closing; the first clip arm or the second clip arm is fixedly connected with an upper side or a lower side of the mounting window by a fixed pull wire; the fixed pull wire sequentially passes through the support base and the connection pipe, and then is fixedly connected with the handle shell; correspondingly, the first clip arm or the second clip arm is movably connected with the lower side or the upper side of the mounting window by a movable pull wire; and the movable pull wire sequentially passes through the support base and the connection pipe, and then is connected with an end portion of the push rod.

In an exemplary embodiment, the handle shell is provided with a button; the push rod is provided with a sliding groove along an axial direction of the push rod; a lower end of the button passes through the sliding groove, and is connected with an elastic reset piece; and when the push rod is pushed to a bottom end of the handle shell, the button is able to pressed down to clamp the push rod.

In an exemplary embodiment, the elastic reset piece is a reset spring; and a button hole corresponding to the button is further formed on the handle shell.

In an exemplary embodiment, a pipe joint is disposed at a corner of one side of the support base; and the support base is connected with the connection pipe by the pipe joint.

In an exemplary embodiment, a wiring groove is formed at periphery of the support base; and the wiring groove communicates with the pipe joint.

In an exemplary embodiment, a plurality of wire passing holes for passing through the fixed pull wire and the movable pull wire are formed in the wiring groove.

In an exemplary embodiment, the connection pipe is a straight pipe or a metal pipe having a predetermined bending angle; and a wire shearing groove is formed at one end, close to the handle shell, of the connection pipe.

In an exemplary embodiment, the connection pipe is formed by a plurality of segments of connection branch pipes connecting sequentially, where one segment of the connection branch pipe is provided with a predetermined bending angle, or the plurality of segments of the connection branch pipes are all straight pipes; and a wire shearing groove is formed at one end, close to the handle shell, of one of the connection branch pipes.

In an exemplary embodiment, the handle shell includes an upper shell and a lower shell; and the upper shell and the lower shell are butted to form the handle shell.

In an exemplary embodiment, the support base is of a mouth shape.

(3) Beneficial effects

Compared with the conventional art, the present disclosure has the following advantages.

In the present disclosure, by adopting the atrial appendage clip delivery system in the above technical solutions, the atrial appendage clip can be conveniently placed from the outside of the heart to the root of the left atrial appendage to close the left atrial appendage in the thoracotomy or minimally invasive surgery; moreover, locking and unlocking functions can be implemented; and therefore, the use is convenient, safe and effective.

Figure 1:
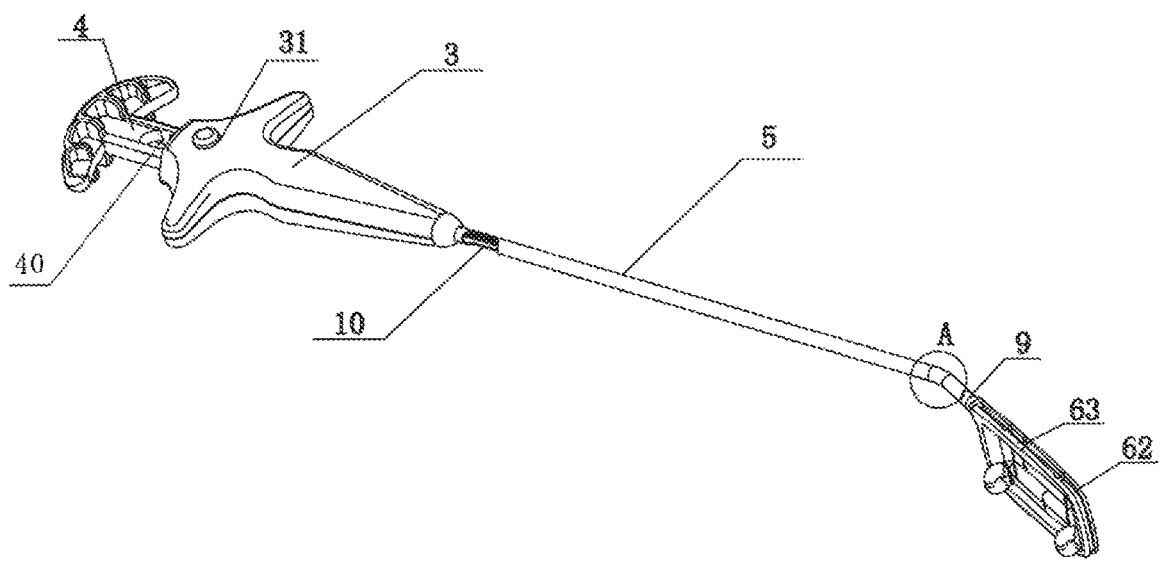
FIG. 1 is a first overall structural schematic diagram of an atrial appendage clip delivery system in the present disclosure.

In the drawings, 1: first clip arm; 2: second clip arm; 3: handle shell; 31: button hole; 32: upper shell; 33: lower shell; 34: button; 4: push rod; 5: connection pipe; 6: support base; 61: mounting window; 62: wiring groove; 63: wire passing hole; 7: movable pull wire; 8: fixed pull wire; 9: pipe joint; 10: wire shearing groove; 40: sliding groove; 51: connection branch pipe.

DETAILED DESCRIPTION OF THE EMBODIMENTS

Specific implementation manners of the present disclosure will be further described below in detail in combination with accompanying drawings and embodiments. The following embodiments are merely for describing the present disclosure, but are not intended to limit a scope of the present disclosure.

In the description of the present disclosure, it is to be noted that, orientation or position relationships indicated by the terms "center", "longitudinal" "transversal", "upper", "lower", "front", "rear", "left", "right", "vertical", "horizontal", "top", "bottom", "inner", "outer", etc. are based on the orientation or position relationships as shown in the drawings, for ease of the description of the present disclosure and simplifying the description only, rather than indicating or implying that the indicated device or element must have a particular orientation or be constructed and operated in a particular orientation. Therefore, these terms should not be understood as a limitation to the present disclosure. In addition, the terms such as "first", "second" and "third" are merely for a descriptive purpose, and cannot be understood as indicating or implying relative importance, or implicitly indicating the number of the indicated technical features.

In the description of the present disclosure, it is to be noted that, unless otherwise specified and defined, the terms "install", "connected with", "connected to" should be comprehended in a broad sense. For example, these terms may be comprehended as being fixedly connected, detachably connected or integrally connected; mechanically connected or coupled; or directly connected or indirectly connected through an intermediate medium, or in an internal communication between two elements. The specific meanings about the foregoing terms in the present disclosure may be understood by those skilled in the art according to specific circumstances In addition, in the description of the present disclosure, "a plurality of", "multiple" and "multiple groups" means two or more, unless otherwise stated.

Figure 2:
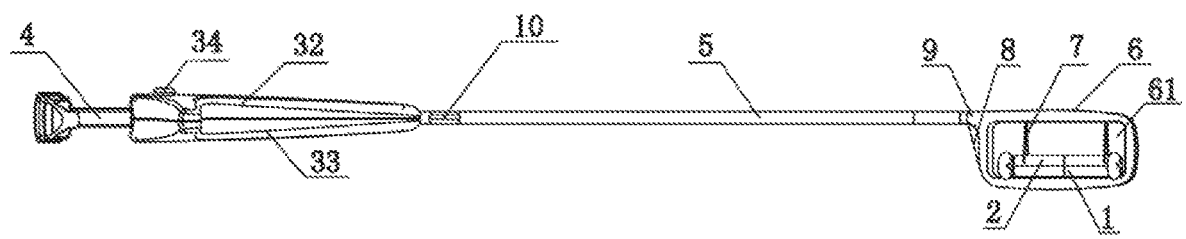
FIG. 2 is a second overall structural schematic diagram of an atrial appendage clip delivery system in the present disclosure.

FIG. 1 and FIG. 2, which show a structural schematic diagram of an atrial appendage clip delivery system provided by the present disclosure. The atrial appendage clip delivery system includes a handle shell 3, a push rod 4, a connection pipe 5 and a support base 6; a passage is provided in the handle shell 3 along a length direction of the handle shell 3; and one end of the push rod 4 is located in the passage, and is slidably and cooperatively connected with the passage.

The connection pipe 5 is a hollow pipeline; one end of the connection pipe 5 is connected with the handle shell 3, and the other end of the connection pipe 5 is connected with the support base 6; and the connection pipe 5, the handle shell 3 and the support base 6 keep communicating.

The support base 6 is provided with a mounting window 61. Specifically, the support base 6 preferably is of a mouth shape disposed in a closed loop, and a circular arc chamfering is provided at periphery of the support base 6; the mounting window 61 is a middle through hole of the mouth-shaped support base 6; and the mounting window 61 is configured to mount an atrial appendage clip.

The atrial appendage clip includes a first clip arm 1 and a second clip arm 2 capable of opening in parallel or closing; a spring is connected between the first clip arm 1 and the second clip arm 2, and is configured to provide an elastic force for opening or closing of the first clip arm 1 and the second clip arm 2; the first clip arm 1 or the second clip arm 2 is fixedly connected with an upper side or a lower side of the mounting window 61 by a fixed pull wire 8, so as to fix the first clip arm 1 or the second clip arm 2 at one side of the mounting window 61; the fixed pull wire 8 sequentially passes through the support base 6 and the connection pipe 5, and then is fixedly connected with the handle shell 3; correspondingly, the second clip arm 2 or the first clip arm 1 is movably connected with the lower side or the upper side of the mounting window 61 by a movable pull wire 7; by pulling the movable pull wire 7, the second clip arm 2 or the first clip arm 1 is driven to move toward the other side of the mounting window 61, so that the atrial appendage clip is opened; and specifically, the movable pull wire 7 sequentially passes through the support base 6 and the connection pipe 5, and then is connected with an end portion of the push rod 4.

As shown in FIG. 1 and FIG. 2, the handle shell 3 is provided with a button 34; the push rod 4 is provided with a sliding groove 40 along an axial direction of the push rod 4; a lower end of the button 34 passes through the sliding groove 40, and is connected with an elastic reset piece; by pushing the push rod 4 with a palm, the sliding groove 40 moves relative to the button 34; and when the push rod 4 is pushed to a bottom end of the handle shell 3, the button 34 is pressed to compress the elastic reset piece such as a reset spring (not shown in figure). The push rod 4 is clamped by using a clamping portion of the button, so that position locking between the handle shell 3 and the push rod 4 is implemented; and at this moment, a maximum distance is opened between the first clip arm 1 and the second clip arm 2. Since the position of the push rod is locked, the atrial appendage clip is kept open and then the opened atrial appendage clip may be conveniently placed to a root of an atrial appendage by the atrial appendage clip delivery system; and after a placement position is confirmed, the button 34 is pressed to relieve the position locking of the push rod 4, and the first clip arm 1 and the second clip arm 2 are closed at a root of a left atrial appendage.

As shown in FIG. 2, a pipe joint 9 is disposed at a corner of one side of the support base 6. An upper surface of the pipe joint 9 is flush with an upper surface of the support base to form a knife handle shaped structure. Since a thoracic cavity is very narrow intrinsically, the pipe joint 9 is attached to one side of the support base (an asymmetric structural design), thereby being more beneficial to inosculation with a heart tissue, preventing the heart tissue such as an aorta and a pulmonary vein from being pressed, and improving the safety in operation.

For the convenience of wiring, a wiring groove 62 is formed at the periphery of the support base 6; the wiring groove 62 communicates with the pipe joint 9; the support base 6 is connected with the connection pipe 5 by the pipe joint 9; and thus, it is convenient for the movable pull wire 7 and the fixed pull wire 8 to be disposed in the pipe joint 9 in a penetration manner from the wiring groove 62 and to enter the connection pipe 5.

Multiple wire passing holes 63 for passing through the fixed pull wire 8 and the movable pull wire 7 are formed in the wiring groove 62; and further, the wire passing holes 63 are symmetrically formed on upper and lower sidewalls of the mounting window 61.

Figure 3:
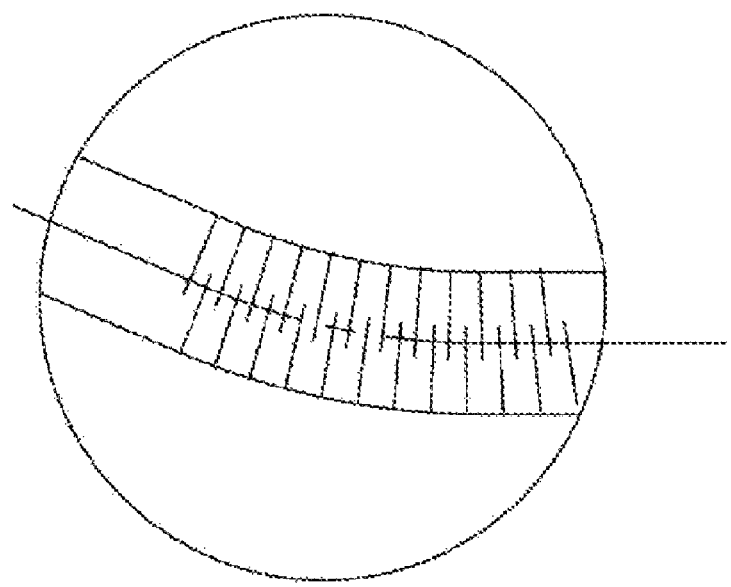
FIG. 3 is a local enlarged diagram of A in FIG. 1.
Figure 4:
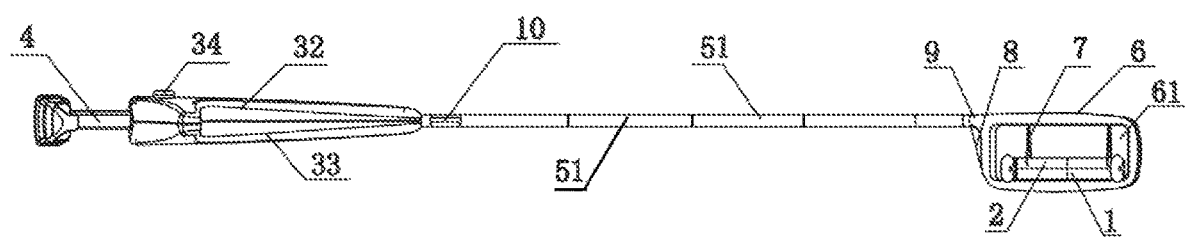
FIG. 4 is a structural schematic diagram of an atrial appendage clip delivery system of another embodiment in the present disclosure.

As shown in FIG. 1 to FIG. 3, the connection pipe 5 may be a segment of complete metal pipe having a predetermined bending angle such as a stainless steel pipe, a nickel-titanium alloy pipe or other medical metal pipes. The predetermined bending angle may be adjusted freely according to a demand, and 360° adjustment without a dead angle may be implemented. Certainly, the connection pipe 5 may also be a segment of straight pipe; or the connection pipe 5 is formed by multiple segments of connection branch pipes 51 connecting sequentially, where one segment of the connection branch pipe 51 may be provided with a predetermined bending angle, e.g. the predetermined angle is bent artificially; the predetermined bending angle may be adjusted freely according to a demand, and 360° adjustment without a dead angle may be implemented. Certainly, the multiple segments of the connection branch pipes 51 may be all straight pipes; and a wire shearing groove 10 is formed at one end, close to the handle shell 3, of the connection pipe 5 or of one of the connection branch pipes 51. After the atrial appendage clip is delivered in place, the movable pull wire and the fixed pull wire are sheared in the wire shearing groove. A pull wire for binding the atrial appendage clip may be sheared in vitro, thereby being convenient for separation of the atrial appendage clip and the delivery system; and by shearing a wire at an outside of the thoracic cavity, an injury to a body of a patient is prevented in a process when the wire is sheared at an inside of the thoracic cavity.

The handle shell 3 includes an upper shell 32 and a lower shell 33. The push rod 4 may be disposed in the lower shell 33 first, and then the upper shall 32 and the lower shell 33 are butted to form the handle shell 3, so that the installation of the push rod 4 is convenient.

The support base 6 may be made of medical polyamide+ 50% glass fiber or other medical nonmetal materials, and may be fixedly connected with the connection pipe 5 by a manner such as sleeving and extruding deformation, gluing and threaded connection.

In the present disclosure, an operation process is as follows: the push rod 4 generates a relative displacement with the handle shell 3 under the action of a pushing force; the movable pull wire 7 fixed on the push rod 4 is moved therewith, and pulls the clip arm at one side of the atrial appendage clip open, so that the two clip arms are opened in parallel; when the push rod 4 is pushed to the bottom end of the handle shell 3, the button 34 is pressed to clamp the push rod 4 and lock the position of the push rod 4; at this moment, a maximum open distance is formed between the clip arms at the two sides of the atrial appendage clip; the atrial appendage clip is stretched into a body of a patient by a wound together with a front end of the atrial appendage clip delivery system; and meanwhile, by virtue of other appliances, the atrial appendage clip sleeves a root of a left atrial appendage; after a placement position is confirmed to be appropriate, the button 34 is pressed manually to relieve the position locking of the push rod 4; at this moment, the clip arms at the two sides of the atrial appendage clip are closed slowly under the action of the spring and the pull wires till the left atrial appendage is attached and is compacted; then, the movable pull wire 7 and the fixed pull wire 8 are sheared at an opening of the wire shearing groove 10; and then, the atrial appendage clip delivery system is taken out from the wound and the rest pull wires winded on the atrial appendage clip are taken out, so that the surgery is implemented completely.

In addition, during the surgery, if a placement direction of the atrial appendage clip cannot meet the surgical demand, the connection pipe may be bent manually by a doctor according to an actual condition so as to achieve a best appropriate angle.

From the above embodiments, it may be seen that with the atrial appendage clip delivery system of the present disclosure, the atrial appendage clip can be conveniently and reliably placed from the outside of the heart to the root of the left atrial appendage to close or even permanently close the left atrial appendage in a thoracotomy or minimally invasive surgery.

The above are only preferred embodiments of the present disclosure and are not intended to limit the present disclosure. Any modification, equivalent replacement and improvement made within the spirit and principle of the present disclosure should be included in a scope of protection of the present disclosure.

What is claimed is:

1. An atrial appendage clip delivery system, comprising a handle shell, a push rod, a connection pipe and a support base, wherein
   a passage is provided in the handle shell along a length direction of the handle shell;
   one end of the push rod is located in the passage, and is slidably and cooperatively connected with the passage;
   the connection pipe is a hollow pipeline; one end of the connection pipe is connected with the handle shell, and the other end of the connection pipe is connected with the support base; a pipe joint is disposed at a corner of one side of the support base; and the support base is connected with the connection pipe by the pipe joint; wherein an upper surface of the pipe joint and an upper surface of the support base are in a same plane, and a center line of the pipe joint in a length direction of the pipe joint deviates from a center line of the support base in a length direction of the support base, such that the pipe joint and the support base form an asymmetric structural design;
   the support base is provided with a mounting window for mounting an atrial appendage clip; and
   the atrial appendage clip comprises a first clip arm and a second clip arm capable of opening in parallel or closing; the first clip arm or the second clip arm is fixedly connected with an upper side or a lower side of the mounting window by a fixed pull wire; the fixed pull wire sequentially passes through the support base and the connection pipe, and then is fixedly connected with the handle shell; correspondingly, the second clip arm or the first clip arm is movably connected with the lower side or the upper side of the mounting window by a movable pull wire; and the movable pull wire sequentially passes through the support base and the connection pipe, and then is connected with an end portion of the push rod.

2. The atrial appendage clip delivery system as claimed in claim 1, wherein the handle shell is provided with a button; the push rod is provided with a sliding groove along an axial direction of the push rod; a lower end of the button passes through the sliding groove, and is connected with an elastic reset piece; and when the push rod is pushed to a bottom end of the handle shell, the button is able to be pressed down to clamp the push rod.

3. The atrial appendage clip delivery system as claimed in claim 2, wherein the elastic reset piece is a reset spring; and a button hole corresponding to the button is further formed on the handle shell.

4. The atrial appendage clip delivery system as claimed in claim 1, wherein a wiring groove is formed at periphery of the support base; and the wiring groove communicates with the pipe joint.

5. The atrial appendage clip delivery system as claimed in claim 4, wherein a plurality of wire passing holes for passing through the fixed pull wire and the movable pull wire are formed in the wiring groove.

6. The atrial appendage clip delivery system as claimed in claim 1, wherein the connection pipe is a straight pipe or a metal pipe having a predetermined bending angle; and a wire shearing groove is formed at one end, close to the handle shell, of the connection pipe.

7. The atrial appendage clip delivery system as claimed in claim 1, wherein the connection pipe is formed by a plurality of segments of connection branch pipes connecting sequentially, wherein one segment of the connection branch pipe is provided with a predetermined bending angle, or the plurality of segments of the connection branch pipes are all straight pipes; and a wire shearing groove is formed at one end, close to the handle shell, of one of the connection branch pipes.

8. The atrial appendage clip delivery system as claimed in claim 1, wherein the handle shell comprises an upper shell and a lower shell; and the upper shell and the lower shell are butted to form the handle shell.

9. The atrial appendage clip delivery system as claimed in claim 1, wherein the support base is of a mouth shape.

10. An atrial appendage clip delivery system, comprising a handle shell, a push rod, a connection pipe and a support base, wherein
   a passage is provided in the handle shell along a length direction of the handle shell;
   one end of the push rod is located in the passage, and is slidably and cooperatively connected with the passage;
   the connection pipe is a hollow pipeline; one end of the connection pipe is connected with the handle shell, and the other end of the connection pipe is connected with the support base;
   the support base is provided with a mounting window for mounting an atrial appendage clip; and
   the atrial appendage clip comprises a first clip arm and a second clip arm capable of opening in parallel or closing; the first clip arm or the second clip arm is fixedly connected with an upper side or a lower side of the mounting window by a fixed pull wire; the fixed pull wire sequentially passes through the support base and the connection pipe, and then is fixedly connected with the handle shell; correspondingly, the second clip arm or the first clip arm is movably connected with the lower side or the upper side of the mounting window by a movable pull wire; and the movable pull wire sequentially passes through the support base and the connection pipe, and then is connected with an end portion of the push rod;
   the connection pipe is a straight pipe or a metal pipe having a predetermined bending angle; and the connection pipe comprises a first end connected with the handle shell and a second end connected with the support base, and a wire shearing groove is formed at the first end of the connection pipe.

11. An atrial appendage clip delivery system, comprising a handle shell, a push rod, a connection pipe and a support base, wherein
   a passage is provided in the handle shell along a length direction of the handle shell;
   one end of the push rod is located in the passage, and is slidably and cooperatively connected with the passage;
   the connection pipe is a hollow pipeline; one end of the connection pipe is connected with the handle shell, and the other end of the connection pipe is connected with the support base;
   the support base is provided with a mounting window for mounting an atrial appendage clip; and
   the atrial appendage clip comprises a first clip arm and a second clip arm capable of opening in parallel or closing; the first clip arm or the second clip arm is fixedly connected with an upper side or a lower side of the mounting window by a fixed pull wire; the fixed pull wire sequentially passes through the support base and the connection pipe, and then is fixedly connected with the handle shell; correspondingly, the second clip arm or the first clip arm is movably connected with the lower side or the upper side of the mounting window by a movable pull wire; and the movable pull wire sequentially passes through the support base and the connection pipe, and then is connected with an end portion of the push rod;
   the connection pipe is formed by a plurality of segments of connection branch pipes connecting sequentially, wherein one segment of the connection branch pipe is provided with a predetermined bending angle, or the plurality of segments of the connection branch pipes are all straight pipes; and the connection pipe comprises a first end connected with the handle shell and a second end connected with the support base, and a wire shearing groove is formed at the first end of the connection pipe.

* * * * *